United States Patent [19]

Lundquist

[11] Patent Number: 5,426,199
[45] Date of Patent: Jun. 20, 1995

[54] CATALYZED ESTERIFICATION PROCESS

[75] Inventor: Eric G. Lundquist, North Wales, Pa.

[73] Assignee: Rohm and Haas Company, Philadelphia, Pa.

[21] Appl. No.: 990,803

[22] Filed: Dec. 14, 1992

Related U.S. Application Data

[63] Continuation-in-part of Ser. No. 807,291, Dec. 13, 1991, abandoned.

[51] Int. Cl.$^6$ .............................................. C11C 3/00
[52] U.S. Cl. .................................... 554/169; 554/170
[58] Field of Search ................. 554/142, 169, 170, 194

[56] References Cited

U.S. PATENT DOCUMENTS

| | | | |
|---|---|---|---|
| 2,678,332 | 5/1954 | Cottle | 260/475 |
| 3,037,052 | 5/1962 | Bortnick | 260/188 |
| 3,252,921 | 5/1966 | Hamsen et al. | 260/2.2 |
| 3,278,585 | 10/1966 | Baker et al. | 260/473 |
| 3,590,073 | 6/1971 | Carr et al. | 260/476 R |
| 3,678,099 | 7/1972 | Kemp | 260/497 |
| 4,221,871 | 9/1980 | Meitzner et al. | 521/29 |
| 4,332,738 | 6/1982 | Benitez et al. | 260/410 |
| 4,652,406 | 3/1987 | Lepper et al. | 260/410.9 |
| 4,698,186 | 10/1987 | Jeromin et al. | 554/174 |

FOREIGN PATENT DOCUMENTS

| | | |
|---|---|---|
| 454792 | 7/1971 | Australia. |
| 310843 | 4/1989 | European Pat. Off. . |
| 3509292 | 5/1986 | Germany. |

OTHER PUBLICATIONS

McMaster et al, Ind. Eng. Chem. Prod. Res. Dev., vol. 11, No. 1 (1972) pp. 97–105.
Widdecke et al., Macromal, Chem. Phys. Suppl., 6 (1984) pp. 211–226.
Journal of Applied Chemistry, vol. 20, No. 4, pp. 101–107, 1970.
Journal of Macromolecular Science, Chemistry, vol. A11, No. 10, 1977.

*Primary Examiner*—José G. Dees
*Assistant Examiner*—Deborah D. Carr
*Attorney, Agent, or Firm*—John E. Taylor, III

[57] ABSTRACT

Esters may be produced with a minimum formation of ether by-product by reacting an organic acid or ester with an alcohol at elevated temperatures in the presence of vinylaromatic polymer beads which are surface functionalized with strongly acidic functional groups, the inner volume of the polymer beads remaining unfunctionalized.

20 Claims, No Drawings

CATALYZED ESTERIFICATION PROCESS

The present application is a continuation-in-part of the U.S. patent application Ser. No. 807,291, filed Dec. 13, 1991, now abandoned.

This invention relates to a process for esterification and transesterification, particularly of organic acids with alcohols or of esters with alcohols, and more particularly to an esterification process catalyzed with surface-functionalized, crosslinked vinylaromatic polymer beads.

BACKGROUND OF THE INVENTION

Strongly acidic cation-exchange resins behave as though they were solid acids in many reactions, and can replace such mineral acids as sulfuric acid and hydrochloric acid as acid catalysts. Because they permit easier product separation, decreased equipment corrosion and expense, and increased product purity, these cation-exchange resins are widely used as catalysts for esterifying acids with alcohols or olefins. For example, see the disclosures in U.S. Pat. Nos. 3,037,052 to Bortnick, 4,332,738 to Benitez et al., 3,278,585 to Baker et al., 3,678,099 to Kemp, 2,678,332 to Cottle and 4,652,406 to Lepper et al. One such esterification reaction, that of inexpensive, naturally occurring palm-oil and coconut-oil fatty acids with alcohols to produce fatty esters,

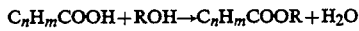

$$C_nH_mCOOH + ROH \rightarrow C_nH_mCOOR + H_2O$$

where $n=8$ to 19 and $m=17$ to 39, is of considerable interest. These fatty esters may be saturated or unsaturated, and may be used as intermediates for producing surfactants and linear detergent alcohols. Esters of lower molecular weight, where $n=1$ to 8 and $m=3$ to 17 have found considerable use as solvents, flavors and fragrances. Another reaction of commercial interest is the esterification of anhydrides with alcohols to produce dialkyl diesters useful in producing diols. Esters of unsaturated acids such as acrylates and methacrylates produced by the esterification of unsaturated acids with alcohols are also of commercial interest. Esters may also be produced by transesterification of esters and alcohols. However, to achieve high organic-acid esterification and transesterification rates when using strongly acidic cation-exchange resins, the water produced by the reaction must be removed, high alcohol concentrations must be used, and the reaction must be conducted at elevated temperatures (e.g. 60° C. to 120° C.). These conditions can produce excellent conversions, but also promote the formation of dialkyl ethers from the acid-catalyzed self condensation of alcohols:

$$ROH + R'OH \rightarrow R\text{—}O\text{—}R' + HOH$$

The formation of these dialkyl ethers not only wastes the alcohol but also creates problems with product separation and waste disposal.

An approach to reduce the amount of byproduct produced in an esterification reaction is described in U.S. Pat. No. 3,678,099, assigned to Chevron Research Company. In this process isobutene was esterified with a carboxylic acid in the presence of a macroporous, acidic cation-exchange resin having a limited cation-exchange capacity (0.2 to 2.4 meq/g, compared with the usual 4–6 meq/g for fully functionalized, macroporous cation-exchange resins); it had the advantage of reducing the amount of isobutene polymerization. The capacity of this macroreticular resin was reduced by partially neutralizing it with sodium ions.

Although surface-functionalized cation-exchange resins have been produced, as for example by McMaster et al., *Ind. Eng. Chem. Prod. Res. Develop.*, Vol. 11, No. 1 (1972), pp. 97–105, who controlled depth of sulfonation to as little as 15% of the total bead diameter by carefully limiting the sulfonation time, and by Widdecke et al., *Macromol. Chem. Phys. Suppl.*, 6 (1984) pp. 211–226, who sulfonated the surface of macroporous resins, such resins have largely remained a laboratory tool for investigating reaction kinetics. Little incentive has existed to use them in industrial processes because of their relatively low cation-exchange capacity, and they are not known as esterification catalysts. Partially sulfonated cation-exchange resins having a cation-exchange capacity between 0.1 and 0.6 meq/g were shown to produce negligible byproducts when used to selectively decompose methyl t-butyl ether to isobutylene and methanol (West German Patent No. DE 3,509,292), and inorganic oxides with modified surfaces have been employed as esterification catalysts for fatty acids (European Patent Application No. EP 310 843), but that reference did not suggest surface functionalization of organic polymer beads with strong-acid functional groups for that purpose.

SUMMARY OF THE INVENTION

I have discovered an esterification process which comprises contacting an organic acid or ester with an alcohol at a temperature of at least about 60° C. in the presence of crosslinked, vinylaromatic polymer beads which have a surface functionalized with strongly acidic functional groups to a cation-exchange capacity of from about 0.1 to about 2.5 meq/g and an inner volume of unfunctionalized polymer.

DETAILED DESCRIPTION OF THE INVENTION

The crosslinked, vinylaromatic polymer beads which have a surface functionalized with strongly acidic functional groups to a cation-exchange capacity of from about 0.1 to about 2.5 meq/g and an inner volume of unfunctionalized polymer, and which are useful in the present invention, act as a catalyst for the esterification reaction of an acid or an ester with an alcohol, and have the particularly advantageous property of favoring the formation of esters over the formation of ethers. In those embodiments of the esterification process of the present invention wherein the alcohol is a secondary or a tertiary alcohol, the surface functionalized catalyst beads have the additional advantageous property of favoring the formation of esters over the formation of olefinic by-products. They are hereinafter termed "surface-functionalized catalyst beads."

The crosslinked, vinylaromatic polymer beads useful for making the surface-functionalized catalyst beads of the present invention include both gel beads and macroporous beads, with the macroporous beads being preferred. These beads are surface functionalized with strongly acidic functional groups to a cation-exchange capacity of from about 0.1 to about 2.5 meq/g. In the case of the gel beads, the surface functionalization is readily understood as functionalization of the outer surface of the beads. In the case of macroporous beads the surface of the bead, as referred to herein, is intended to include the surfaces of the macropores which are internal to the bead itself. This concept of a surface internal to the bead is readily understood by those skilled in the art, because macroporous beads are known to possess a surface area much greater than that accounted for by the external surface of the bead, and that additional surface area is understood to be contributed by the internal surfaces of the macropores. It is the polymer forming that internal surface, as well as polymer at the actual, outer surface of the bead, that is functionalized to produce the macroporous beads useful in the present invention.

The terms "surface functionalization" and "surface functionalized" are intended to refer to functionalized polymeric materials with a limited functionality which occurs at or near the surface of the polymer, and is not necessarily restricted to only the surface layer of aromatic nuclei. The depth of functionalization of the surface-functionalized catalyst beads is severely restricted, however, by limiting the functionality to about 2.5 meq/g or less, and by functionalizing the beads in a manner that will promote functionalization from the surface inward, so that only the first few layers of aromatic nuclei are functionalized. Such functionalizations are known to those skilled in the art, being taught by, e.g., Hansen et al, U.S. Pat. No. 3,252,921.

While not wishing to be bound by theory, I have found evidence that indicates the strongly acidic functional groups that are more distant from the surface of the polymer contribute more to the formation of ethers during the esterification of organic acid with alcohols, while those closest to the surface are responsible for most of the esterification. I believe that the surface functional groups are accessible to all the reactants, while the functional groups deeper within the polymer are accessible only to small, polar reactants. When fully functionalized polymer beads are used in esterification reactions, the non-polar, organic acid and small, polar alcohol partition themselves differently within the strong acid ion exchange resin catalyst. The polar alcohol partitions into the interior of the hydrophilic polymer, which is not accessible to the non-polar, organic acid. The high concentration of alcohol and low concentration of organic acid at the functional groups within the hydrophilic polymer causes the formation of ethers through alcohol condensation. In the esterification of an organic acid with a secondary or tertiary alcohol, the high concentration of alcohol within the interior of a fully functionalized polymer bead also favors a second type of undesirable side reaction, i.e., dehydration of the alcohol to form olefinic by-products. Dehydration of the alcohol to form olefinic by-products is wasteful of the valuable alcohol. The olefinic by-products so formed contaminate the product ester and can foul the polymer beads, shortening the useful life of the beads as catalysts. Accordingly, I believe the surface-functionalized catalyst beads useful in the present invention to be those which minimize formation of ethers and other undesirable byproducts while maximizing formation of esters. I believe those catalyst beads to contain aromatic nuclei bearing strongly acidic functional groups only at or near the polymer surface, with the remainder of the aromatic nuclei being unfunctionalized.

The formation of crosslinked, vinylaromatic polymer beads by suspension polymerization is well known to those skilled in the art. Formation of such beads containing macroporosity is similarly well known, and several approaches have been disclosed for preparing them. Preferred for making the crosslinked, vinylaromatic polymer beads which are precursors to the surface-functionalized catalyst beads of the present invention is the procedure disclosed by Meitzner et al. in U.S. Pat. No. 4,221,871, which produces a particular type of macroporous bead known as a macroreticular bead.

Preferred as monomers to be polymerized in making the crosslinked, vinylaromatic polymer beads useful in the present invention are vinylaromatic monomers such as styrene and substituted styrenes such as $\alpha$-methylstyrene, vinyltoluene and the like, vinylnaphthalene and substituted vinylnaphthalenes, and mixtures thereof. Small amounts, up to about 20% by weight of the monomers, of vinylaliphatic monomers may be present, but as these contain no functionalizable aromatic nuclei, they tend to reduce the overall catalytic activity of the surface-functionalized catalyst beads. The polymer beads which result from polymerizing the monomer or mixture of monomers are crosslinked. This crosslinking comprises methylene bridges or other crosslinks that form during functionalization or other post-polymerization reactions, and it may be augmented by the introduction into the monomer mixture of crosslinking monomers, that is, those containing more than one polymerizable vinyl group. Preferred are polyvinylaromatic monomers such as divinylbenzene, trivinylbenzene, divinylnaphthalene and the like, but one or more polyvinylaliphatic monomers may also be present as the crosslinking monomer, as for example ethylene glycol dimethacrylate, trimethylolpropane trimethacrylate and the like. Crosslinking monomers may be introduced at levels from about 1 to about 100 weight percent of the total monomer. In the case of the crosslinked, polyvinylaromatic polymer beads which are made largely or entirely from crosslinking monomers, the preferred monomers are the polyvinylaromatic monomers described above. Preferred are polymers made from monomer mixtures containing from about 2 to about 25 weight percent polyvinylaromatic polymers.

Strongly acidic functional groups useful for functionalizing the vinylaromatic polymer beads to make the surface-functionalized catalyst beads of the present invention include sulfonic and phosphonic acid groups and their respective salts, and preferably the sulfonic acid groups and their salts. Critical to the present invention is that the functional groups be located at or near the surface of the polymer, whether this be the external surface or, in the case of macroporous beads, the internal surface of the polymer beads. Methods for restricting functionalization to the surface of the polymer are known to those skilled in the art. Most of these depend upon the fact that a functionalizing agent, as for example sulfuric acid or chlorosulfonic acid, penetrates polymer beads from the surface at a regular rate, functionalizing aromatic nuclei as it penetrates, to create a shell of relatively uniform thickness in which the aromatic nuclei are largely or entirely functionalized. By proper choice of conditions, including the functionalizing reagent and whether and which swelling solvents are used, the rate at which the functionalizing agent penetrates and functionalizes the beads is kept slow enough that the penetration depth may be monitored. The functionalization is halted after it has proceeded to the desired depth, which is sufficient to produce a cation-exchange capacity of from about 0.1 to about 2.5 meq/g, by quenching in water or by other methods which will be apparent to those skilled in the art.

The esterification process of the present invention involves esterification or transesterification of an organic acid or ester with an alcohol. The organic acid may be mono-, di- or polycarboxylic; it may be a linear or branched, aliphatic or aromatic, saturated or unsaturated hydrocarbon acid, or it may be an alkaryl or aralkyl acid, again with the aliphatic portion being saturated, unsaturated, linear or branched. The organic acid may also have one or more of its hydrogens substituted by halogen, nitro or other similar groups. The corresponding anhydrides of these acids may also be employed in the process of the present invention. The preferred acids have from two to twenty carbon atoms including the carboxyl carbon. Examples of such acids are acetic, propionic, butyric, valeric, caproic, caprylic, capric, stearic, oleic, linolenic and arachidic acids; acrylic, methacrylic, crotonic, vinylacetic and other unsaturated acids; oxalic, malonic, succinic, maleic, glutaric, adipic, sebacic, phthalic, isophthalic, trimellitic, pyromellitic, 1,2,3,4-butanetetracarboxylic, fumaric, tartaric and other similar polycarboxylic acids; benzoic, toluic, phenylacetic, diphenylacetic, cinnamic, hydrocinnamic, phenylpropionic and similar aromatic acids, substituted acids such as trifluoroacetic, fluoroacetic, chloroacetic, α-chloropropionic, methoxyacetic, β-ethoxypropionic, p-chlorobenzoic and 2,4-dichlorophenoxyacetic acids; and anhydrides such as acetic, propionic, butyric, maleic, stearic, succinic, benzoic, phthalic, pyromellitic and naphthalic anhydrides and pyromellitic dianhydride.

The alcohols, both those used in the esterification and transesterfication reactions, and those which contribute the alcohol portion of the esters which are transesterified, again may be alcohols of linear or branched, aliphatic, aromatic, alkaryl or aralkyl hydrocarbons, and the preferred alcohols may have from one to twenty carbon atoms. The alcohols may be primary, secondary or tertiary; they may be mono-, di- or polyols; and they may also have one or more of their hydrogens substituted by halogen, nitro, ether or other similar groups, so long as these groups do not interfere, at the chosen reaction conditions, with the esterification reaction, as by causing competing reactions such as alcoholysis, hydrolysis or other hydrolytic displacement at the substituent group. Examples of such alcohols are methanol, ethanol, n-propanol, isopropanol, butanols such as n-butanol; pentanols such as n-pentanol, isopentanol or cyclopentanol; hexanols such as n-hexanol, cyclohexanol or methyl isobutyl carbinol; heptanols, benzyl alcohol, octanols, lauryl alcohol, cetyl alcohol, stearyl alcohol, ethylene glycol, diethylene glycol, triethylene glycol, propylene glycol, dipropylene glycol, butylene glycol, 1,2,3,4-butanetetrol, glycerine, glycerol monomethyl ether, glycerol monoethyl ether, 1,5-pentanediol, 1,3,5-pentanetriol, 1,6-hexanediol, hexanetriols such as 1,2,6-hexanetriol; hexanetetrols, hexanehexols such as dulcitol, mannitol and sorbitol; and branched analogs of any of the above.

The esterification process of the present invention, utilizing the surface-functionalized catalyst beads described above, is carried out by contacting an organic acid with an alcohol in the presence of the surface-functionalized catalyst beads. The reaction temperature for the process is preferably at least about 60° C. As the reaction temperature is reduced, the amount of ether produced by the reaction is also reduced, but so is the reaction rate of the desired, esterification reaction. Consequently, while the surface-functionalized catalyst beads useful in the present invention may catalyze esterification at temperatures below about 60° C., the advantage of their selectivity is reduced in comparison with other acidic catalysts at such low temperatures, and the reaction rates become impractically slow. A more preferred reaction-temperature range is from about 60° C. to about 130° C.; although the reaction proceeds readily, and with the stated advantages, at higher temperatures, above about 130° C. the catalyst beads may tend to degrade excessively. It would be obvious to one of ordinary skill in the art to use, in the process of the present invention, higher temperatures with surface-functionalized beads having adequate thermal stability at temperatures above 130° C. A more preferred reaction-temperature range is from about 70° C. to about 120° C., and a still more preferred range is from about 80° C. to about 110° C. While atmospheric pressure is preferred for the reaction, pressures above or below atmospheric may be used, and this may be desirable in certain situations to help control the temperature or maintain a reagent in the liquid state. The reagents and surface-functionalized catalyst beads are allowed to remain in contact until the desired degree of conversion has been achieved, which is generally from about 0.25 to about 16 hours, and preferably from about one to about eight hours.

Although the esterification or transesterification reaction in the process of the present invention will proceed over a wide range of reactant ratios, as for example over the alcohol:ester or acid ratio range from about 0.5:1 to about 20:1 on a molar basis, it is favored by an excess of alcohol over the organic acid. A more preferred range for the ratio of alcohol:acid or ester is from about 1:1 to about 15:1 on a molar basis, and a still more preferred range is from about 2:1 to about 10:1 on a molar basis. The alcohol and acid or ester may be mixed in the presence of the surface-functionalized catalyst beads, or mixed and subsequently added to them, or the beads added to the mixture. The reaction mixture may be heated to the reaction temperature prior or subsequent to mixing the reagents or contacting them with the surface-functionalized catalyst beads, but whenever the alcohol, acid and beads are present simultaneously and the temperature is 60° C. or greater, the alcohol:acid ratio is preferably at least about 0.5:1, and more preferably at least about 1:1.

Because the esterification is an equilibrium reaction, the water produced during the reaction is preferably removed to favor formation of the ester. The water may be removed by boiling, distillation, adsorption with an adsorbing agent that is relatively non-reactive with the alcohol, organic acid or ester, or by other processes which will readily be apparent to those skilled in the art. The preferred method of removing the water is maintaining the reaction temperature above the boiling point of water or a water azeotrope at the pressure employed, thereby allowing the water or water azeotrope to boil off continuously.

EXAMPLES

The following examples are intended to illustrate the invention and not to limit it, except as it is limited in the claims. All ratios, percentages and proportions are by weight unless otherwise specified, and all reagents used are of good commercial quality unless otherwise specified.

Example 1

This example illustrates synthesis of a surface-sulfonated catalyst resin of the present invention.

To a 5 liter three necked flask equipped with a condenser, mechanical stirrer and a thermocouple was added 400 g dry, macroporous, styrene-20% divinylbenzene copolymer beads. To this flask was added 100 ml ethylene dichloride and 2000 g 96% sulfuric acid. The copolymer was allowed to swell in this mixture for one hour, after which the mixture was heated to 45° C. and held at that temperature for 1.5 hours to sulfonate the copolymer. At the end of that time a quench of 1000 ml cold, distilled water was added to the mixture to halt the sulfonation; the mixture was cooled to prevent the temperature from rising above 65° C. during addition of the quench water. The ethylene dichloride was removed by steam distillation and the sulfonated material was washed with water and then with methanol. This material had an acid capacity of 1.30 meq/g and a moisture-holding capacity of 44%. This surface sulfonated material of the present invention is referred to below as Catalyst D.

Example 2

This example illustrates another synthesis of a surface-sulfonated catalyst resin of the present invention.

To a 3-liter, 3-necked flask equipped with a condenser, mechanical stirrer and a thermocouple was added 200 g dry, macroporous, styrene-20% divinylbenzene copolymer beads, 100 g of glacial acetic acid and 2000 g of sulfuric acid. The copolymer beads were allowed to swell in this mixture for one hour, then the mixture was heated to 50° C. and held at that temperature for two hours to allow the copolymer to sulfonate. After this sulfonation, 500 ml of cold, deionized water was added to quench the reaction, with cooling as necessary to prevent the temperature from rising above 65° C. This material had an acid capacity of 1.15 meq/g and a moisture-holding capacity of 38%. This material is referred to below as catalyst F. Table I, below, shows the physical properties of Catalysts D and F of the present invention, with three other, fully sulfonated, macroporous catalysts (A, B and C) and a fully sulfonated gel catalyst (E) which are employed in subsequent examples as comparative catalysts of the prior art.

TABLE I

| Catalyst | Copolymer Crosslinker Level, Wt. % | Acid wt. capacity, meg/g | Surface area, m²/g | Porosity, ml/g |
|---|---|---|---|---|
| A | 12 | 5.0 | 35 | 0.24 |
| B | 20 | 4.7 | 43 | 0.35 |
| C | 80 | 3.3 | 450 | 0.45 |
| D | 20 | 1.3 | 45 | 0.35 |
| E | 4 | 5.2 | NA[1] | NA[1] |
| F | 20 | 1.1 | 45 | 0.35 |

[1]Catalyst E is a gel resin with only microporosity; it contains no macroporosity, and its surface area is approximately that of a sphere having the same diameter as the catalyst beads.

Example 3

This example illustrates the process of the present invention as applied to the esterification of lauric acid with methanol.

To separate flasks containing 70 g melted lauric acid were added 7 g samples of the pre-dried, sized (425-600 μm), strongly acidic, cation-exchange resin catalysts of Table I. The contents of the flasks were heated to 110° C. and maintained at that temperature while methanol was added at a rate of 0.4 ml per minute. A temperature of 110° C. was also maintained above the liquid to remove the methanol and the water produced by the reaction. The reaction was monitored by removing a 3-ml sample of the reaction mixture every 30 minutes, dissolving it in 10 ml methanol and then titrating the residual acid with a standardized solution of sodium hydroxide. The amount of dimethyl ether produced was determined by trapping the gas in 2-butoxyethanol and determining the dimethyl ether gas chromatographically, and was confirmed by measuring the volume of gas evolved from the reaction and using the ideal gas law to calculate the number of moles of dimethyl ether produced. The gas chromatographic results of these esterification reactions are shown in Table II, below.

TABLE II

| | Lauric Acid Esterification Results | |
|---|---|---|
| Catalyst | Time to 99.5% conversion, min. | Dimethyl ether produced at 99.5% conversion, grams |
| A | 180 | 3.80 |
| B | 165 | 3.40 |
| C | 160 | 1.80 |
| D | 156 | 1.00 |

Example 4

This example illustrates the process of the present invention as applied to the esterification of monomethyl maleate with methanol.

To a fixed-bed reactor containing 57 ml of a strongly acidic, cation exchange resin catalyst of Table I was fed continuously a mixture containing 38.89% methanol, 59.58% monomethyl maleate, 0.99% dimethyl maleate and 0.32% water. The reaction was repeated for each catalyst, and the amount of dimethyl maleate and dimethyl ether produced by the reaction were determined. The results of these reactions are shown in Table III, below.

TABLE III

| Catalyst | Temp. | LHSV, HRS-1 | Product Conversion % | Dimethyl ether in product, wt. % |
|---|---|---|---|---|
| A | 60° C. | 0.25 | 99.20 | 0.21 |
| D | 60° C. | 0.25 | 99.20 | 0.06 |

Example 5

This example illustrates the process of the present invention as applied to the esterification of lauric acid with n-butanol.

To separate flasks containing 70 g melted lauric acid were added 7 g portions of the pre-dried, strong-acid cation exchange resin catalysts of Table I, screened to a size range of 590-840 μm. The contents of the flasks were heated to 110° C. and maintained at that temperature while n-butanol was added at a rate of 0.4 ml per minute. A temperature of 110° C. was also maintained above the liquid to remove butanol and water produced by the reaction. The progress of the reaction was monitored by removing 3-ml samples of the reaction mixture every 60 minutes, dissolving it in 10 ml butanol and titrating the solution for residual acid using a standardized aqueous sodium hydroxide solution. The amount of dibutyl ether produced was determined by measuring both the dibutyl ether content of the reaction flask and the dibutyl ether content of the distillate by gas chromatography. The lauric acid conversion and amount of dibutyl ether produced are shown in Table V, below.

TABLE IV

| Catalyst | Time mins | Lauric Acid Conversion % | Dibutyl Ether Produced (ppm) |
|---|---|---|---|
| A | 180 | 97.82 | 260 |
| D | 180 | 97.90 | 180 |

Example 6

This example illustrates the process of the present invention as applied to the esterification of stearic acid with n-butanol.

The procedure of Example 5 was followed, substituting 70 g melted stearic acid for the lauric acid,. The temperature to which the flask contents and the vapor above the liquid were heated was 120° C. The stearic acid conversion and amount of dibutyl ether produced are shown in Table V, below.

TABLE V

| Catalyst | Time mins | Stearic Acid Conversion % | Dibutyl Ether Produced (ppm) |
|---|---|---|---|
| A | 180 | 98.80 | 410 |
| D | 180 | 99.43 | 220 |

Example 7

This example illustrates the process of the present invention as applied to the esterification of acrylic acid with butanol using a continuously fed, stirred-tank reactor with a fixed catalyst bed.

To a continuously fed, stirred-tank reactor containing 82 g of the catalyst of the present invention at a temperature of 90° C. was fed a mixture of n-butanol and glacial acrylic acid having proportions shown in Table VI, below as "BuOH:AA Ratio", the ratio of n-butanol to acrylic acid. As the reaction proceeded, the water produced by the esterification reaction was continuously removed by distillation. The conversion of acrylic acid, as the percentage of acrylic acid convened to butyl acrylate, and the rate of production of dibutyl ether were determined gas chromatographically, and the selectivities were calculated as parts dibutyl ether produced per million pans butyl acrylate produced; these are shown in Table VI, below.

TABLE VI

| Catalyst | BUOH:AA Ratio | Feed Rate (ml/hr) | Acrylic Acid Conversion, % | Selectivity (ppm DBE) |
|---|---|---|---|---|
| C | 1.00:1 | 100 | 88.39 | 3884 |
| C | 1.00:1 | 300 | 67.38 | 2062 |
| C | 1.00:1 | 500 | 52.06 | 1230 |
| D | 1.00:1 | 100 | 81.12 | 794 |
| D | 1.00:1 | 300 | 58.91 | 548 |
| D | 1.00:1 | 500 | 44.86 | 485 |
| E | 1.00:1 | 100 | 90.47 | 1710 |
| E | 1.00:1 | 300 | 80.77 | 1858 |
| E | 1.00:1 | 500 | 70.76 | 828 |
| B | 1.35:1 | 100 | 87.90 | 4383 |
| B | 1.35:1 | 300 | 64.20 | 2452 |
| B | 1.35:1 | 500 | 45.78 | 1792 |

Example 8

This example illustrates the process of the present invention as applied to transesterification of methyl methacrylate with n-butanol to form n-butyl methacrylate. This reaction is represented by the reaction:

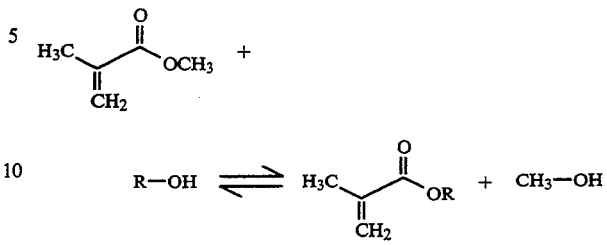

in which the R—OH is n-butanol.

The equipment used for the transesterification reaction was a continuous loop reactor operated in an open-system mode, that is, during the reaction the methanol produced is continuously removed as a methanol-methyl methacrylate azeotrope. This reactor comprises a heated, stirred, 250-ml, round-bottom flask equipped with a temperature controller, a sparge tube connected to a 92% nitrogen gas source, a drain tube connected to the bottom of the flask, and a distillation head. The drain tube was arranged to feed a pump which circulated the reaction mixture from the flask through a reaction column containing the catalyst resin and back into the flask at a rate of 200 ml/minute. The distillation head contained a controller which allowed continuous, automatic removal of a portion of the azeotroped vapors above the reaction mixture. The reaction column contained 67 g of the catalyst resin being tested, and was held at 100° C. A mixture of n-butanol and methyl methacrylate, in an 0.83:1 alcohol:ester molar ratio, was fed continuously into the circulation path of the reaction mixture, ahead of the reaction column, at a rate of 2 ml/minute. The catalyst of the present invention produced an n-butanol conversion percentage, based on the feed rate, of 40.3%, and a rate of butyl methacrylate formation of 2.3 millimoles n-butyl methacrylate per gram of catalyst per hour.

Example 9

This example illustrates the process of the present invention as applied to a batch transesterification of n-butyl acetate with n-hexanol to form n-hexyl acetate.

To a stirred reactor equipped with thermocouple and condenser trap was added 12 g catalyst resin beads (Catalyst F) which had been dried for 12 hours at 100° C. under vacuum. To this was added 110 g n-hexanol (99.9% purity) and the reaction mixture was heated to 80° C. At that temperature 25 g n-butyl acetate (99% purity) were added and the mixture was heated to 120° C. and held at that temperature for two hours to allow the transesterification reaction to proceed. During the reaction, evolved butanol was collected in the condenser trap. At the end of the 2-hour reaction period the reaction mixture was cooled to ambient temperature and filtered to remove the catalyst beads. The reacted mixture was analyzed gas chromatographically, and the results are shown in Table VII, below.

TABLE VII

| Catalyst | % Conversion of butyl acetate | % Dibutyl ether in product | % Dihexyl ether in product |
|---|---|---|---|
| A | 87 | 3.11 | 2.97 |
| F | 86 | 1.79 | 0.59 |

As may be seen from Table VII, the catalyst resin useful in the process of the present invention (F) is surprisingly superior to fully sulfonated catalyst resins in suppressing formation of ether, while producing an equivalent yield of ester.

Example 10

This example illustrates the process of the present invention as applied to direct esterification of methacrylic acid with n-butanol using the continuous-loop, open-system reactor described in Example 7. The procedure of Example 7 was repeated, using a mixture of n-butanol and methacrylic acid, in a 1.2:1 alcohol:acid molar ratio, and 134 g catalyst resin in the reaction column. Remaining conditions and results are shown in Table VIII, below.

TABLE VIII

| Catalyst | Temp, °C. | Flow Rate, ml/min | Rate of BuMA Formation, mmol/g/hr | Rate of DBE Formation mmol/g/hr | % MAA Conversion at steady state |
|---|---|---|---|---|---|
| B | 90 | 180 | 4.1 | 0.027 | 59.1 |
| F | 90 | 180 | 3.9 | 0.003 | 56.4 |
| B | 100 | 120 | 3.8 | 0.048 | 83.8 |
| F | 100 | 120 | 3.6 | 0.004 | 79.9 |

This example shows the surprising selectivity of the present process for formation of butyl methacrylate over formation of dibutyl ether. This selectivity is better by an order of magnitude for the present process, using resin F, than for the prior-art process using fully sulfonated resin B.

Example 11

This example illustrates a batch procedure of the present invention for esterifying methacrylic acid with n-butanol.

Using an apparatus similar to that of Example 3, the reaction flask was charged with 152 g glacial methacrylic acid, 157 g n-butanol and 67.3 g catalyst beads. The reaction mixture was initially heated to 85, and the temperature was allowed to rise to a maximum of 95° C. during the reaction. The reaction was repeated in triplicate, for Catalyst F of the present invention, and for Catalyst C, the fully sulfonated catalyst of the prior art The results for this example are shown in Table IX, below.

TABLE IX

| Catalyst | Reaction Time, hrs | % Methacrylic Acid Conversion | % DBE Produced |
|---|---|---|---|
| F | 6 | 97.0 | 0.058 |
| F | 6 | 88.2 | 0.050 |
| F | 6 | 90.0 | 0.041 |
| C | 7 | 93.2 | 0.237 |
| C | 7 | 86.1 | 0.265 |
| C | 7 | 88.6 | 0.355 |

Again, these results show that the reaction is surprisingly selective for the production of the ester over the dibutyl ether, when compared with the fully sulfonated resins.

These examples show clearly that when the surface-sulfonated cation-exchange resin of the present invention is employed in the esterification process of the present invention, a significant reduction is observed in the amount of ether produced in the reaction.

Example 12

This example illustrates the process of the present invention vs. applied to the esterification of 2-ethylhexanol with acetic acid.

Catalyst beads of the present invention (catalyst F described above) were dried for 12 hours at 100° C. under vacuum. A 5 g sample of the dried catalyst beads was introduced into a stirred reactor. The reactor was equipped with a thermocouple and a condenser trap. The flask was then charged with 50 g 2-ethylhexanol (99% purity) and the contents of the flask were then heated to 110° C. The flask was then charged with 15 g glacial acetic acid and the temperature was maintained at 110° C. for a reaction period of 2 hours following the acid charge. Water generated during the reaction was collected in the condenser trap. At the end of the 2 hour reaction period the product mixture was allowed to cool to ambient temperature and then filtered to remove the catalyst beads. The product mixture was analyzed by gas chromatography.

The reaction was repeated using the above method, but substituting each of two fully sulfonated catalysts (Catalysts A and C, described above in Example 2) for catalyst F.

Results of the chromatographic analyses are set forth below in Table X for the product esters made using the respective catalysts as % conversion of acetic acid and at the combined amount (ppm) of 2-ethyl-1-hexene and 2 ethyl-2-hexene in each of the respective product esters.

I claim:

1. A process for producing esters with a low content of ethers which comprises contacting an organic acid or ester with an alcohol at a temperature of at least about 60° C. in the presence of crosslinked, vinylaromatic polymer beads which are surface-functionalized with strongly acidic functional groups to a cation-exchange capacity of from about 0.1 to about 2.5 meq/g and an inner volume of unfunctionalized polymer.

2. The process of claim 1 wherein an organic acid is contacted with the alcohol to esterify the acid.

3. The process of claim 1 wherein an organic ester is contacted with the alcohol to transesterify the ester.

4. The process of claim 1 wherein the cation-exchange capacity is from about 0.1 to about 2.0 meq/g.

5. The process of claim 1 wherein the cation-exchange capacity is from about 0.1 to about 0.6 meq/g.

6. The process of claim 1 wherein the beads are gel polymer beads.

7. The process of claim 1 wherein the beads are macroporous polymer beads.

8. The process of claim 1 wherein water produced by the reaction is continuously removed during the process.

9. The process of claim 1 wherein the temperature is from about 60° C. to about 130° C.

10. The process of claim 1 wherein the temperature is from about 70° C. to about 120° C.

11. The process of claim 1 wherein the temperature is from about 80° C. to about 110° C.

12. The process of claim 1 wherein the alcohol and acid or ester are present in a molar ratio of alcohol:acid or alcohol:ester of from about 0.5:1 to about 20:1.

13. The process of claim 1 wherein the alcohol and acid or ester are present in a molar ratio of alcohol:acid or alcohol:ester of from about 1:1 to about 15:1.

14. The process of claim 1 wherein the alcohol has from one to twenty carbon atoms.

15. The process of claim 2 wherein the organic acid has from two to twenty carbon atoms.

16. The process of claim 3 wherein the ester has an acid component of from two to twenty carbon atoms.

17. The process of claim 3 wherein the ester has an alcohol component of from one to twenty carbon atoms.

TABLE X

| CATALYST | % CONVERSION OF ACETIC ACID | 2-ETHYL-1-HEXENE AND 2 ETHYL-2-HEXENE IN PRODUCT ESTER (PPM) |
| --- | --- | --- |
| A | 93 | 164 |
| C | 88 | 61 |
| F | 94 | 2 |

18. The process of claim 1, wherein the alcohol is a secondary alcohol or a tertiary alcohol.

19. The process of claim 2, wherein the alcohol is a secondary alcohol or a tertiary alcohol.

20. The process of claim 3, wherein the alcohol is a secondary alcohol or a tertiary alcohol.

* * * * *